US009826918B2

(12) United States Patent
Eberl et al.

(10) Patent No.: US 9,826,918 B2
(45) Date of Patent: Nov. 28, 2017

(54) METHOD AND DEVICE FOR DETECTING THE SURFACE STRUCTURE AND PROPERTIES OF A PROBE

(71) Applicant: Juergen Marx, Koblenz (DE)

(72) Inventors: Heinrich Alexander Eberl, Immenstadt (DE); Juergen Marx, Koblenz (DE)

(73) Assignee: Juergen Marx, Koblenz (DE)

( * ) Notice: Subject to any disclaimer, the term of this patent is extended or adjusted under 35 U.S.C. 154(b) by 0 days.

(21) Appl. No.: 14/898,931

(22) PCT Filed: Aug. 28, 2015

(86) PCT No.: PCT/EP2015/069768
§ 371 (c)(1),
(2) Date: Mar. 14, 2016

(87) PCT Pub. No.: WO2017/036498
PCT Pub. Date: Mar. 9, 2017

(65) Prior Publication Data
US 2017/0059308 A1    Mar. 2, 2017

(51) Int. Cl.
*A61B 5/103* (2006.01)
*G01S 17/89* (2006.01)
(Continued)

(52) U.S. Cl.
CPC .......... *A61B 5/1032* (2013.01); *A61B 5/1172* (2013.01); *A61B 5/1455* (2013.01);
(Continued)

(58) Field of Classification Search
CPC .................................................. A61B 5/1032
See application file for complete search history.

(56) References Cited

U.S. PATENT DOCUMENTS 5,726,443 A    3/1998   Immega et al.
5,877,688 A    3/1999   Morinaka et al.
(Continued)

FOREIGN PATENT DOCUMENTS

DE    19601854 C1    7/1997
DE    19858750 A1    6/1999
(Continued)

OTHER PUBLICATIONS

Crane et al., "Infrared Spectroscopic Imaging for Noninvasive Detection of Latent Fingerprints", Journal of Forensic Sciences, Jan. 2007, pp. 48-53, vol. 52, No. 1.
(Continued)

*Primary Examiner* — David Porta
*Assistant Examiner* — Hugh H Maupin
(74) *Attorney, Agent, or Firm* — The Webb Law Firm (57) ABSTRACT

A method for detecting the surface structure and composition of a sample by means of a scanning unit, in particular for detecting traces, which are induced by contact of the skin of the human body on the surface of an object or absorbed by means of a trace carrier. The sample and the scanning unit are moved in relation to one another. The sample surface is irradiated line-by-line using a light beam or laser beam emitted from the scanning unit. The light beam or laser beam reflected from the sample surface is detected, and a digital image of the topography of the sample surface and the intensity of the reflected light beam or laser beam is generated from deviations of the reflected light beam or laser beam from the emitted light beam or laser beam to illustrate the composition of the sample surface.

20 Claims, 11 Drawing Sheets

(51) Int. Cl.

| | | |
|---|---|---|
| G01N 21/3563 | (2014.01) | |
| A61B 5/1172 | (2016.01) | |
| A61B 5/1455 | (2006.01) | |
| A61B 5/00 | (2006.01) | |
| G01B 11/24 | (2006.01) | |
| G01S 17/02 | (2006.01) | |
| G01S 17/42 | (2006.01) | |
| G01S 7/48 | (2006.01) | |
| H04N 5/33 | (2006.01) | |
| H04N 5/225 | (2006.01) | |
| H04N 3/09 | (2006.01) | |
| G01N 21/47 | (2006.01) | |
| G01N 21/84 | (2006.01) | |
| G01S 7/481 | (2006.01) | |

(52) U.S. Cl.
CPC ............ *A61B 5/441* (2013.01); *A61B 5/6826* (2013.01); *G01B 11/24* (2013.01); *G01N 21/3563* (2013.01); *G01S 7/4802* (2013.01); *G01S 17/023* (2013.01); *G01S 17/42* (2013.01); *G01S 17/89* (2013.01); *A61B 2562/0238* (2013.01); *A61B 2576/00* (2013.01); *G01N 21/4738* (2013.01); *G01N 21/8422* (2013.01); *G01N 2201/06113* (2013.01); *G01N 2201/105* (2013.01); *G01N 2201/12* (2013.01); *G01S 7/4817* (2013.01); *H04N 3/09* (2013.01); *H04N 5/2256* (2013.01); *H04N 5/33* (2013.01)

(56) References Cited

U.S. PATENT DOCUMENTS

| | | | |
|---|---|---|---|
| 6,081,612 A | 6/2000 | Gutkowicz-Krusin et al. | |
| 6,130,958 A | 10/2000 | Rohler et al. | |
| 6,154,564 A | 11/2000 | Hashemi | |
| 6,363,173 B1 | 3/2002 | Stentz et al. | |
| 6,404,904 B1 | 6/2002 | Einighammer et al. | |
| 6,898,299 B1 | 5/2005 | Brooks | |
| 2002/0057438 A1* | 5/2002 | Decker ............ | G01B 11/2509 356/601 |
| 2004/0022417 A1 | 2/2004 | Nishigaki et al. | |
| 2004/0047493 A1 | 3/2004 | Rowe et al. | |
| 2004/0179723 A1 | 9/2004 | Sano et al. | |
| 2004/0256541 A1 | 12/2004 | Cofer et al. | |
| 2006/0056661 A1 | 3/2006 | Einighammer et al. | |
| 2006/0214121 A1* | 9/2006 | Schrey ................... | G01S 7/481 250/559.38 |
| 2006/0269896 A1* | 11/2006 | Liu .......................... | A61C 7/00 433/29 |
| 2007/0047796 A1 | 3/2007 | Anantharaman | |
| 2007/0081156 A1* | 4/2007 | Treado ..................... | G01J 3/02 356/301 |
| 2007/0183633 A1 | 8/2007 | Hoffmann | |
| 2009/0250611 A1 | 10/2009 | Strandemar | |
| 2010/0315628 A1 | 12/2010 | Mertsching et al. | |
| 2011/0032507 A1 | 2/2011 | Braunecker et al. | |
| 2011/0085708 A1 | 4/2011 | Martin et al. | |
| 2011/0135164 A1 | 6/2011 | Maurer et al. | |
| 2013/0140463 A1 | 6/2013 | Myrick et al. | |
| 2015/0181137 A1 | 6/2015 | Terashima et al. | |
| 2015/0304552 A1* | 10/2015 | Matsuzaki ............ | G02B 21/18 348/80 |
| 2016/0011049 A1* | 1/2016 | Furstenberg ............... | G01J 3/02 356/456 |
| 2016/0026845 A1* | 1/2016 | Miesak ............... | G06K 9/00013 382/124 |

FOREIGN PATENT DOCUMENTS

| | | |
|---|---|---|
| DE | 19818229 A1 | 10/1999 |
| DE | 19830058 A1 | 12/1999 |
| DE | 19951320 A1 | 4/2001 |
| DE | 1058811 T1 | 6/2001 |
| DE | 69704485 T2 | 9/2001 |
| DE | 10022143 A1 | 11/2001 |
| DE | 10128717 A1 | 12/2002 |
| DE | 69905175 T2 | 1/2004 |
| DE | 10306576 A1 | 8/2004 |
| DE | 102004011480 A1 | 10/2004 |
| DE | 69820337 T2 | 11/2004 |
| DE | 69633524 T2 | 3/2005 |
| DE | 69730053 T2 | 7/2005 |
| DE | 102004039937 A1 | 2/2006 |
| DE | 60020606 T2 | 3/2006 |
| DE | 60021738 T2 | 6/2006 |
| DE | 102004063745 B3 | 9/2006 |
| DE | 102006053540 B3 | 1/2008 |
| DE | 602004009793 T2 | 8/2008 |
| DE | 102008037741 A1 | 2/2010 |
| DE | 102008039643 A1 | 3/2010 |
| DE | 10026586 B4 | 4/2010 |
| DE | 102010041497 A1 | 3/2012 |
| DE | 112010003414 T5 | 12/2012 |
| DE | 102011111168 A1 | 2/2013 |
| DE | 112011101562 T5 | 2/2013 |
| WO | 2006000552 A1 | 1/2006 |
| WO | 2009033220 A1 | 3/2009 |

OTHER PUBLICATIONS

Froehlich et al., "Active Laser Radar (LIDAR) for measurement of corresponding height- and reflectance images", SPIE Proceedings, Aug. 1997, pp. 292-305, vol. 3101.

Jimenez et al., "Automatic fruit recognition: a survey and new results using Range/Attenuation images", Pattern Recognition, 1999, pp. 1719-1736, vol. 32.

Manabe et al., "Simultaneous Measurement of Spectral Distribution and Shape", Pattern Recognition, 2000, pp. 803-806.

* cited by examiner

METHOD AND DEVICE FOR DETECTING THE SURFACE STRUCTURE AND PROPERTIES OF A PROBE

CROSS-REFERENCE TO RELATED APPLICATIONS

This application is the United States national phase of International Application No. PCT/EP2015/069768 filed Aug. 28, 2015, the disclosure of which is hereby incorporated in its entirety by reference.

BACKGROUND OF THE INVENTION

Field of the Invention

The invention relates to a method for detecting the surface structure and composition of a sample and a device for detecting the surface structure and composition of a sample.

The method according to the invention and the device for detecting the surface structure and composition of a sample by means of a scanning unit can advantageously be used for detecting traces, which are induced by contact of the skin of the human body on the surface of the object or are absorbed by means of a trace carrier, in medical technology for incident light observation during skin cancer examinations, and in the industrial field for detecting surface coatings and for thickness measurement of internal layers of an object.

Description Of Related Art

A device for detecting an imprint on a trace carrier is known from DE 10 2011 111168 A1, which contains a trace carrier support, a receptacle head having a camera, which records infrared beams, and a mount for the receptacle head, using which the receptacle head is mounted in relation to the trace carrier holder. The infrared camera records the infrared beams which are emitted and/or reflected from an imprint on the trace carrier. The receptacle head is arranged in a mount, which contains a telescoping column for setting the distance of the receptacle head from the trace carrier, which can be linearly moved horizontally along a bar held by two bars. The receptacle head additionally has a digital camera for preparing images of an evidence object deposited on the trace carrier and an infrared emitter, which can be moved in a circle about the infrared camera.

The restriction of the scanning surface of the trace carrier to the dimensions of the bar arrangement for moving the receptacle head and the risk of distortions and shading during the scanning of an imprint on the trace carrier and corruption of the scanned images as a result of external light incident on the imprint are disadvantageous in this case.

A method for detecting a fingerprint is known from DE 100 22 143 A1, in which an image of the fingerprint arranged on a trace carrier is recorded in the invisible, infrared wavelength range by means of a camera, so that the image results, not only as in the visible wavelength range due to the reflection or absorption of the incident light, but rather also due to the emitted thermal radiation. For this purpose, the trace carrier is placed on a temperature-regulated supporting surface and irradiated by a light source, which is arranged laterally and offset in height in relation to the temperature-regulated supporting surface. The image is recorded by means of a camera, which is arranged above the trace carrier located on the temperature-regulated supporting surface. The trace carrier is illuminated using light of the desired wavelength range by way of the arrangement of spectral filters on the light source and the camera.

This arrangement for detecting an imprint on a trace carrier has the disadvantage that due to the arrangement of the light source, shading occurs on the structured surface of the imprint as well as nonvisible regions due to the position and the conical field of vision of the camera, which make it necessary to record the imprint at various viewing angles, to be able to calculate a complete three-dimensional image from individual partial images.

SUMMARY OF THE INVENTION

The present invention is based on the stated problem of providing a method and a device for detecting the surface structure and composition of a sample, which enable, in a scanning procedure having high resolution, distortion-free and shading-free recordings of the topography and the intensity image of a sample and, if needed, a color image (RGB image) with at least theoretically unlimited size of the sample surface.

The method according to the invention ensures that, using a single scanning procedure, the topography of a sample and an intensity image, which characterizes the chemical substances on and in the surface, of the sample is detected with high resolution and distortion-free and shading-free with at least theoretically unlimited size of the sample surface, ensures reliable function even in the event of incident external light, and if needed enables recordings of a color image (RGB image).

By way of the line-by-line scanning of the sample surface, distortion-free and shading-free recording at high resolution of both the topography of the sample surface and also the intensity of the reflected light beam and therefore the composition of the sample or the chemical substances contained in the sample or sample surface is ensured. The individual pixels of the line-by-line scanning can therefore be assembled to form an informative digital image of the topography of the sample surface and intensity of the reflected light beam to evaluate the composition of the sample or the chemical substances contained in the sample or sample surface.

The light beam emitted from the scanning unit is either emitted at a wavelength which corresponds to the wavelength range of a previously ascertained significant absorption peak of the chemical substance to be detected on the sample surface, or the scanning unit is configured such that the light beam emitted from the scanning unit is light emitted or tuned in a range of the infrared spectrum. The first-mentioned case is based upon the knowledge of the absorption peak of the sample to be examined, while in the second-mentioned case, a "prescan" takes place to ascertain the absorption peak of the sample or chemical substance.

The sample surface is preferably irradiated line-by-line using a laser beam having predefined laser beam diameter of preferably less than or equal to 0.1 mm in a step width corresponding to the laser beam diameter, the reflected laser beam is detected coaxially in relation to the emitted laser beam, and the run time of the laser beam reflected from the sample surface is analyzed to prepare a distance image corresponding to the topography of the sample surface and the deviation of the laser beam reflected from the sample surface from the laser beam emitted from the scanning unit is analyzed to prepare an intensity image corresponding to the chemical substance on and in the sample surface.

Due to the use of a scanning unit, which is designed in particular as an IR laser scanner, in conjunction with a collimation lens which delimits the laser beam diameter, a high resolution is ensured in the detection of chemical substances on the sample surface, while the detection of the reflected light beam coaxially in relation to the emitted light beam ensures distortion-free and shading-free scanning for optimum illustration and analysis of the sample surface.

To ascertain the topography of the sample surface, either the run time, which is dependent on the distance of the scanning unit from the sample surface, of the laser beam, which is emitted from the scanning unit and reflected from the sample surface, is detected and analyzed to form a distance image corresponding to the topography of the sample surface, or the phase shift between the laser beam emitted from the scanning unit and the laser beam reflected from the sample surface is detected and analyzed to ascertain the topography of the sample surface.

Using this method, the thickness of internal layers of a sample, which differ from external layers, can also be analyzed.

The light beam or laser beam emitted from the scanning unit is preferably sinusoidally modulated and, to determine the phase shift between the light beam or laser beam emitted from the scanning unit and reflected from the sample surface, the reflected light beam or laser beam detected by the scanning unit is correlated with a reference signal synchronous with the emitted light beam or laser beam.

In a preferred embodiment, the sample surface is scanned serially point-by-point using the modulated light beam or laser beam and image elements of a digital image are emulated from the distance and intensity measurements arranged in a matrix.

To prepare an RGB image, the reflected light beam or laser beam can be detected by means of an RGB sensor to ascertain the color values of the scanned sample surface, processed in an RGB image computer unit, and displayed on a display screen.

A device for detecting the surface structure and composition of a sample contains
  a sample receptacle,
  a scanning unit having
    a light source for emitting a light beam having the wavelength range of a known or previously ascertained significant absorption peak of the chemical substance, or for ascertaining the significant absorption peak, a light beam is tuned in a range of the infrared spectrum,
    a receiver for receiving the light beams transmitted or reflected from the sample surface, and
    an X-Y axis deflection unit, which scans the sample surface using the light beams emitted from the light source, and
  an analysis unit having
    a first computer unit for generating a topographic distance image of the sample surface having the chemical substance,
    a second computer unit for generating an infrared image, which depicts the intensity of the reflected light beams, of the sample surface having the chemical substance, and
    a central computer unit which is connected bidirectionally to a memory, a display screen, and the first and second computer units.

To change the distance between the sample receptacle and the scanning unit, the sample receptacle and/or the scanning unit is/are connected to a Z axis drive unit, which is connected bidirectionally via a Z axis driver unit to the central computer unit.

To generate an RGB image as a supplement to the distance and intensity image, an RGB image recording unit, which is oriented onto the sample surface, can be provided, which is connected bidirectionally via a third computer unit to the central computer unit.

While the light source of the scanning unit orients the emitted light beams via a transmitting lens and the X-Y axis deflection unit onto the sample surface, the light receiver of the scanning unit, which preferably contains an infrared photodiode receiver, is connected on the receiving side, which records the reflected light beams, to a receiving lens.

In one preferred embodiment, the scanning unit contains an infrared laser emitter, which orients an IR laser beam via a modulator, which is activated by laser activation electronics, onto a collimator, which emits the IR laser beam with limited laser beam diameter onto a deflection unit, which preferably consists of a polygonal deflection mirror driven by an electric motor, and which deflects the IR laser beam line-by-line onto the sample and deflects the IR laser beams reflected from the sample surface to a photodiode.

A beam splitter, which is arranged in the beam path between the collimator and the deflection unit, transmits the IR laser beams emitted from the collimator to the deflection unit, on the one hand, and deflects the IR laser beams, which are serially combined by the deflection unit and are reflected from the sample surface, to the photodiode.

The IR laser beams, which are fanned out line-by-line by the deflection unit, and the reflected IR laser beams received by the deflection unit are conducted via a correcting lens and a redirection mirror to the sample, wherein at least a part of the IR laser beams, which are fanned out line-by-line by the deflection unit, are deflected onto a synchronization photodiode.

BRIEF DESCRIPTION OF THE DRAWINGS

The fundamental concept of the invention is to be explained in greater detail on the basis of an exemplary embodiment illustrated in the drawing. In the figures.

DETAILED DESCRIPTION OF THE INVENTION

Figure 1:
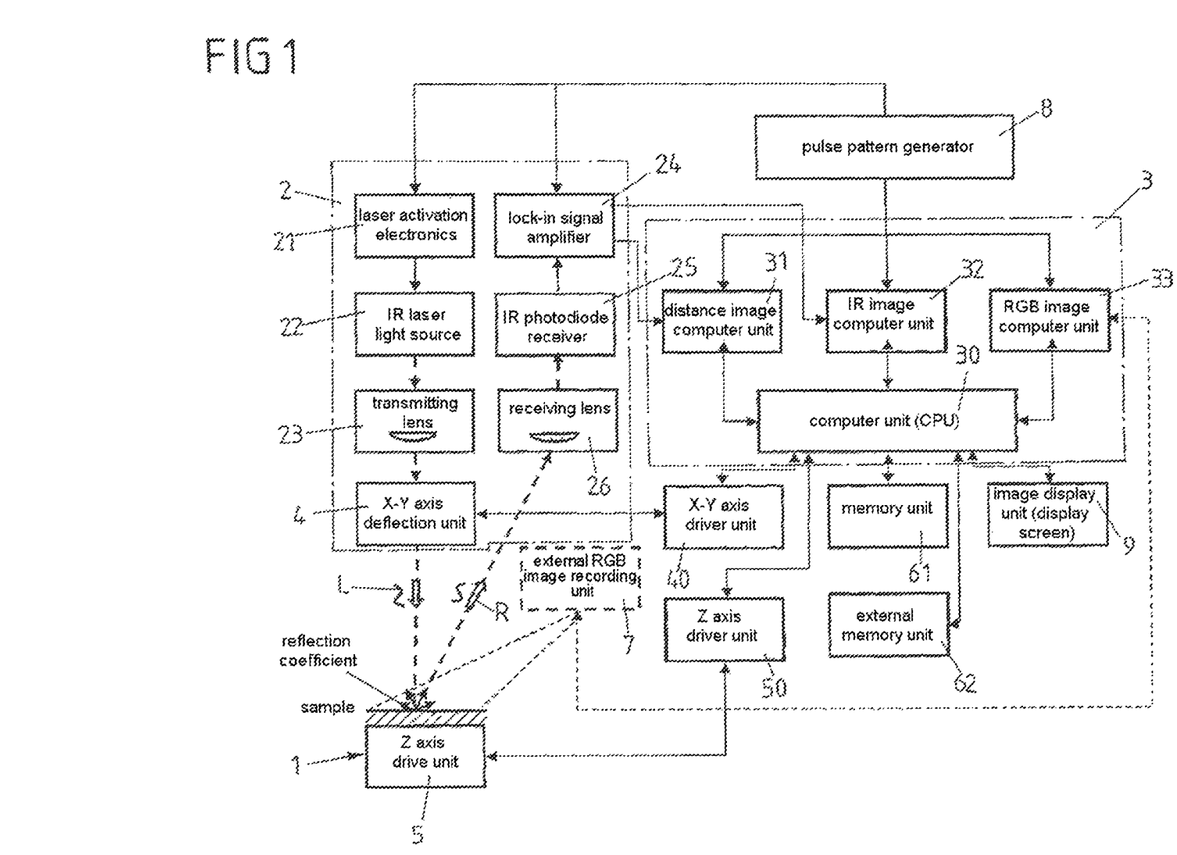
FIG. 1 shows a block diagram of a scanning and analysis unit having an integrated RGB sensor.

FIG. 1 shows a block diagram of a device for detecting the surface structure and composition of a sample or a measured object P. The sample or the measured object P is arranged on a sample receptacle 1, which is connected to a Z axis drive unit 5 for setting the distance between a scanning unit 2 and the sample receptacle 1. The scanning unit 2, which is framed by dot-dash lines, consists of a transmitter having an IR laser light source 22, laser activation electronics 21, and a transmitting lens 23, and a receiver having an IR photodiode receiver 25, a lock-in signal amplifier 24, and a receiving lens 26.

The IR laser light source 22 is activated by the laser activation electronics 21, which are clocked by a pulse generator 8. The laser beams L emitted from the IR laser light source 22 are collimated by means of the transmitting lens 23, tier example, in the form of a collimator, to a laser beam diameter of less than or equal to 0.1 mm, and oriented on the sample P located on the sample receptacle 1. The sample surface is traversed, line-by-line by means of the laser beam L in a step width corresponding to the laser beam diameter and the laser beam R reflected from the sample surface is received by the receiving lens 26 and emitted, to the IR photodiode receiver 25, which is connected on the output side to the lock-in signal amplifier 24, which outputs the amplified measurement signals to an analysis unit 3, which is framed by dot-dash lines, having a first computer unit 31 for calculating a distance image corresponding to the topography of the sample surface and a second computer unit 32 for calculating an intensity image corresponding to the chemical substance of the sample surface, and which is also clocked by the pulse generator 8. The first and second computer units 31, 32 are connected bidirectionally to a central computer unit (CPU) 30, to which a memory unit 61 and, an external memory unit 62 are connected bidirectionally.

The laser beams L emitted from the transmitter 21, 22, 23 of the scanning unit 2 are emitted in the wavelength range in the absorption spectrum of the sample P to be studied. Alternatively, the transmitter 21, 22, 23 emits broadband laser beams in the infrared spectrum to the sample surface, wherein the wavelength is changed or tuned in ranges in 0.2 nm steps.

The laser beam emitted from the IR laser light source 22 is oriented in the transmitting lens 23, collimated to a diameter of less than or equal to 0.1 mm, onto the sample surface and traversed line-by-line by means of a deflection unit, for example, by means of a polygonal mirror or galvanometer, in a step width corresponding to the beam diameter so that by means of the deflection unit, scanning of the sample surface takes place in one axis (X axis) and, by way of the advance of the sample or the scanning unit, in the other axis (Y axis) for scanning the X-Y surface.

An X-Y axis deflection unit 4, which either moves the scanning unit 2 or the sample receptacle 1 in the X-Y plane perpendicular to the Z axis, causes the entire region of the sample surface to be scanned by means of the scanning unit 2. Sample surfaces up to a width of 10 m and arbitrary length can be scanned by the line-by-line scanning of the sample surface in conjunction with the X-Y axis displacement.

The X-Y axis deflection unit 4 is activated by an X-Y axis driver unit 40 and outputs position signals thereto. The X-Y axis driver unit 40 is bidirectionally connected to the central computer unit 30. The Z axis drive unit 5 is activated by a Z axis driver unit 50 and outputs height position signals thereto, wherein the Z axis driver unit 50 is also bidirectionally connected to the central computer unit 30.

To ascertain color values of the sample surface scanned by the scanning unit 2, an external RGB image recording unit 7 can additionally be provided, which is oriented onto the sample surface and is connected to a third computer unit 33, which is also bidirectionally connected to the central computer unit 30.

To detect the topography or contour of the sample surface and composition of the chemical substance of the sample P, the run time of the laser light signals or laser light pulses is measured, which is dependent on the distance of the individual points of the contour of the sample surface, so that an exact depiction of the topography of the sample surface is detected by the calculation of a distance image.

Since the chemical substance to be studied has specific absorption properties, the strength or intensity of the reflected laser beam R supplies a statement about the composition or nature of the sample or sample surface. Therefore, an intensity image of the sample surface can be detected and analyzed from the individual intensity measurement points during the scanning of the sample surface. For this purpose, each individual measurement point can be depicted, for example, in the form of an intensity scale from 0 to 100, wherein an easily recognizable reproduction of the intensity image and corresponding imaging depiction on an image display unit or a display screen 9 is enabled by an assignment of different color scales to the intensity values.

Figure 2:
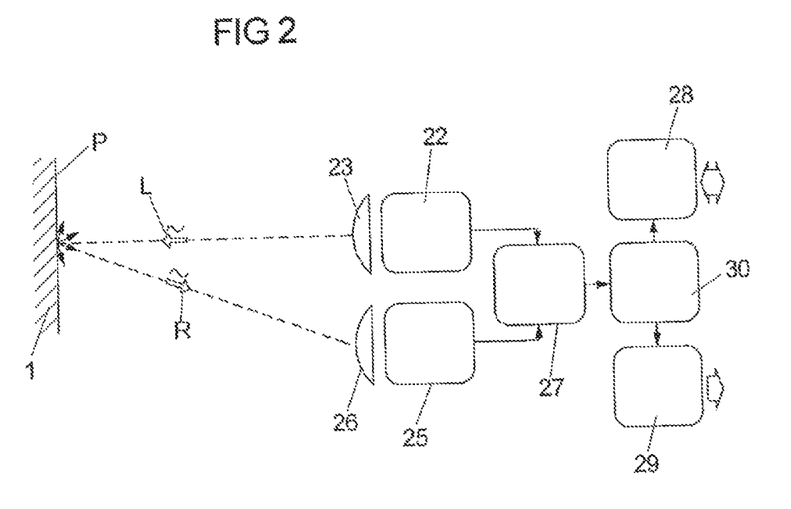
FIG. 2 shows a block diagram of the scanning and analysis unit to explain the functional principle of the optical pulse run time measurement.
Figure 3:
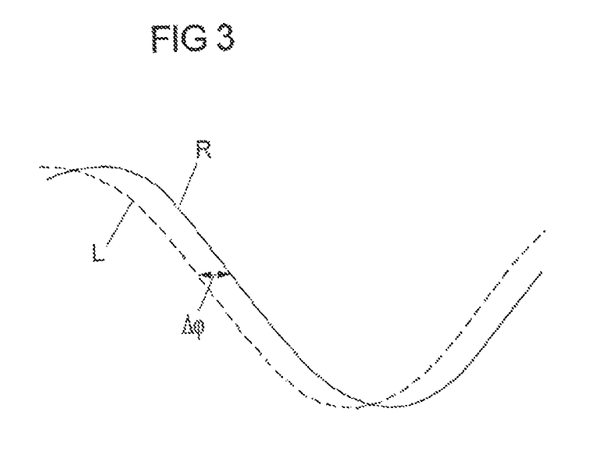
FIG. 3 shows the time curve of an emitted light beam or laser beam and a reference light beam or laser beam to explain a phase difference measurement.

The measurement of the distance between the individual points of the sample surface and the scanning unit 2, which is required for ascertaining the topography of the sample surface, is to be explained in greater detail hereafter on the basis of FIGS. 2 and 3.

FIG. 2 shows a schematic block diagram to explain the functional principle of an optical pulse run time measurement (TOF—time of flight). Similarly to the block diagram according to FIG. 1, a laser light source 22 is provided, the emitted laser beams L of which are oriented, collimated by a transmitting lens 23, onto the sample surface of the sample P located on the sample receptacle 1. The reflected laser beams R are received by the receiving optics 26 and emitted to a photodiode receiver 25. Both the laser light source 22 and also the photodiode receiver 25 emit output signals to a time measurement unit 27, which is connected on the output side to a microprocessor 300. A digital output 28 and optionally an analog output 29 of the measurement unit is/are connected to the microprocessor 300.

The laser light source 22 triggers the time measurement unit 27 simultaneously with the emission of a laser light pulse L. The laser light pulse L is incident on the sample surface, is reflected therefrom, and is received as reflected laser light pulse R by the receiving lens 26 and detected by the photodiode receiver 25, which stops the time measurement unit 27, so that the distance-dependent signal run time was measured, which corresponds directly to the distance of the respective measurement point of the sample surface from the scanning unit 2.

Because only slight differences in the distance-dependent signal run time of the laser beam are measured in the case of very flat contours of the sample surface, the accuracy of the detection, analysis, and reproduction of the topography of the sample surface is dependent on the accuracy of the time measurement. For this reason, a method for distance measurement by means of phase shift is alternatively used, the functional principle of which is shown in FIG. 3 and which makes use of essentially the same device as in FIG. 2, in that a phase measurement unit is used instead of the time measurement unit 27.

In this method, the phase shift is measured, which the optically modulated measurement signal experiences as a result of its path-dependent signal run time in relation to a reference signal. In this case, the laser light pulse in the case of the optical pulse run time measurement is replaced by a sinusoidally modulated signal, the phase of which is determined in that the signal received by the photodiode receiver 25 is correlated with a synchronous reference signal. The phase shift or phase difference Δcp thus ascertained is proportional to the run time of the laser light pulse from the laser light source 22 to the photodiode receiver 25.

To get from the above-described one-dimensional run time measurement to a three-dimensional distance measurement, the sample surface is scanned with the aid of the modulated laser light beam with the aid of the scanning unit 2 and the sample surface is measured serially point-by-point. The measurement results, which are arranged in a matrix, are image elements of a digital image, which reproduces a distance image and therefore the topography of the sample surface and an intensity image of the sample surface, which corresponds to the composition of the sample surface. If an RGB sensor is additionally used, an RGB image can additionally be prepared from the ascertained color values of the measured points.

The measurement data, namely the distance values, intensity values, and RGB color values, are transferred via the interface between the scanning unit 2 and the analysis unit 3 according to FIG. 1 to the analysis unit 3, for example, a PC or laptop, in which they are assembled with the aid of software to form a distance, intensity, and optionally true color image and are visualized on the image display unit or the display screen 9.

In addition to the visual depiction of the measurement data, the analysis unit 3 also causes the recording control of the scanning unit 2, for example, the selection of the region of the sample surface to be scanned, specification of the step width during the scanning procedure, height setting of the sample receptacle 1, etc.

Figure 4:
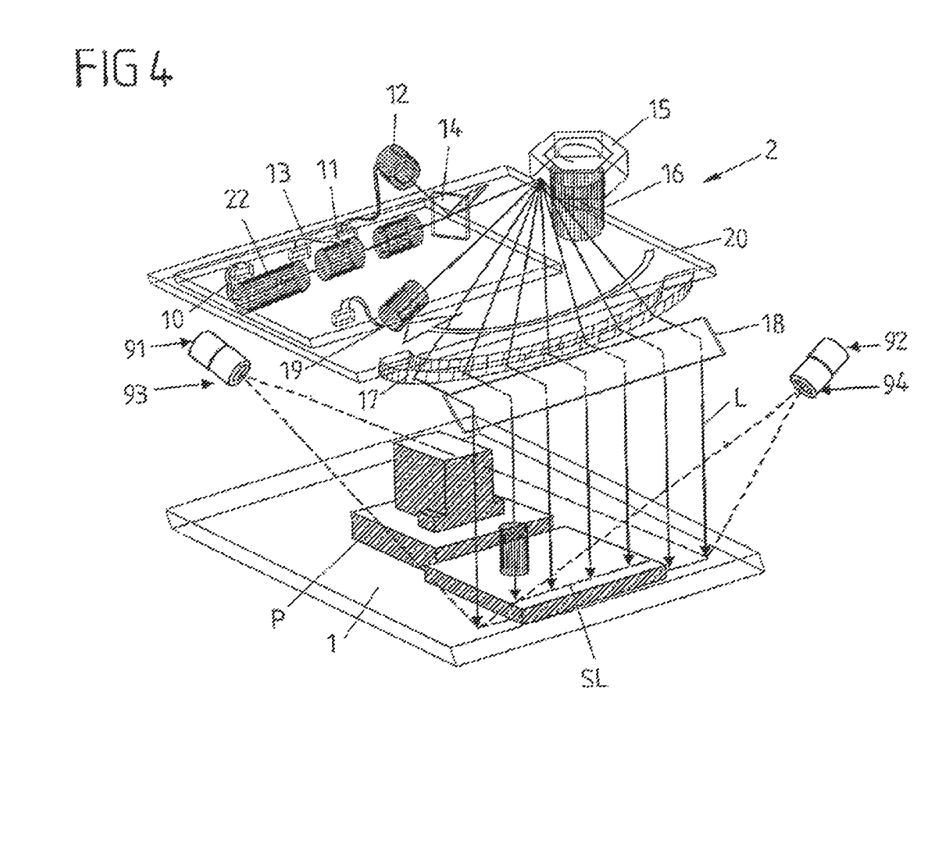
FIG. 4 shows a schematic illustration of the design of a scanning unit having an illustration of the optical beam path.

FIG. 4 shows a schematic illustration of an exemplary embodiment of the device according to the invention and the optical beam path for scanning a three-dimensionally structured sample P, which is arranged on a sample receptacle 1.

The scanning unit 2 contains, on a circuit board 20, the laser light source 22, which is connected via a line 10 to a voltage supply, a modulator 11, which is arranged in the beam path of the laser beam emitted from the laser light source 22, and which is connected via a control line 101 to the laser activation electronics (not shown in greater detail), and a collimator 13, which is arranged in the beam path of the laser beam, and which collimates the laser beam to a diameter of 1 mm or less, in particular less than or equal to 0.1 mm, and orients it through a semitransparent mirror 14 onto a polygonal deflection mirror 15. The polygonal deflection mirror 15, which is driven by an electric motor 16, deflects the laser beam onto a correcting lens 17, wherein the laser beam is deflected over the length of the correcting lens 17 as a result of the rotation of the polygonal deflection mirror 15, which is schematically indicated by the arrow shown.

The semitransparent mirror 14, which is arranged in the beam path between the collimator 11 and the polygonal deflection mirror 15, transmits the laser beams L emitted from the collimator 11 to the polygonal deflection mirror 15, on the one hand, and deflects the laser beams R, which are serially combined by the polygonal deflection mirror 15 and are reflected from the sample surface, to an image recording photodiode 12.

A synchronization photodiode 19 is used for synchronizing the emitted laser beam L with the reflected laser beam R and is also initiated by the laser beam deflected from the polygonal deflection mirror 15. The laser beam, which describes one line at a time, is oriented via a redirection mirror 18 onto the sample P located on the sample receptacle 1 to detect the topography of the sample surface and the composition thereof, which is determined by the absorption properties of the sample surface and corresponds to an intensity image assembled from individual intensity measurement points.

The laser beam R reflected from the sample surface is guided via the redirection mirror 18 and the correcting lens 17 to the rotating polygonal deflection mirror 15, by which the reflected laser beam R is redirected through the semitransparent mirror 14 to the image recording photodiode 12.

FIG. 4 shows the scanning line SL, which is scanned by the scanning unit, so that the topography and composition of the sample P are detected in an axial direction (X axis), while to detect the entire sample surface, the sample receptacle 1 or the scanning unit 2 is moved perpendicularly thereto (Y axis), so that a two-dimensional image is prepared pixel-by-pixel, which is expanded by detecting the run time or phase shift of the IR laser light L into the third dimension, i.e., the topography of the sample P.

In addition, IR detectors 91, 92 having objectives 93, 94 positioned in front of them are positioned diagonally in relation to the sample receptacle 1, wherein one IR detector 91 is oriented along the Y axis, while the other IR detector 92 is oriented perpendicularly thereto along the X axis.

Figure 5:
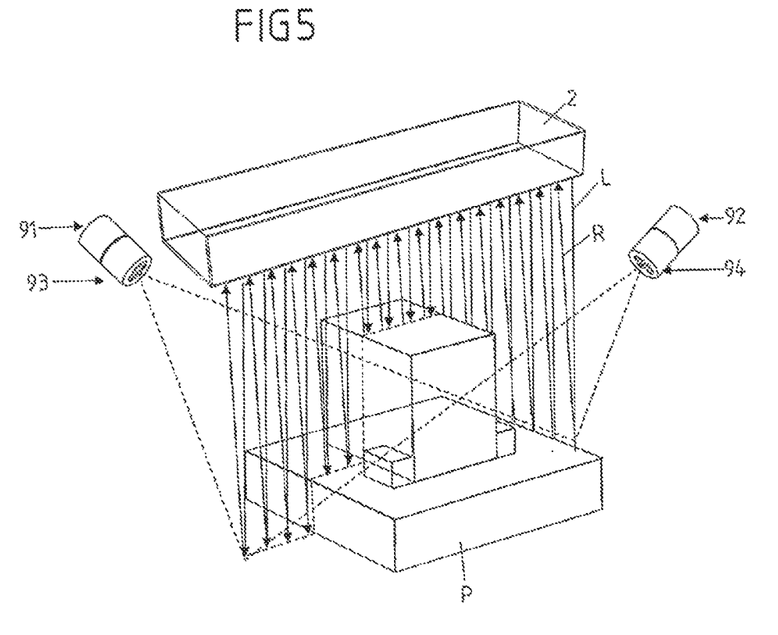
FIG. 5 shows a schematic illustration of the parallel beam path of the modulated light beam or laser beam, which is emitted from the scanning unit, and the reflected modulated light beam or laser beam.

FIG. 5 shows, also in a schematic illustration, the fundamental function of the scanning unit 2 for emitting the modulated IR laser beam L and for receiving the reflected modulated IR laser beam R, the run time or phase shift of which in relation to the modulated IR laser beam L are joined together to determine a distance image and therefore to determine the topography of the surface of the sample P, and the absorption properties thereof and therefore the chemical composition thereof are joined together to form an intensity image.

The IR detectors 91, 92 and objectives 93, 94 are positioned diagonally in relation to the sample receptacle 1, wherein one IR detector 91 is oriented in the Y direction and the other IR detector 92 is oriented in the X direction.

The solution according to the invention enables the layer thickness of a chemical substance to be concluded via the intensity measurement at each measurement point, which can also be used, in addition to the fields of application mentioned at the outset, for the measurement of material coatings, adhesive layers on films, and, in multilayered structures, also internal layers. Examples of this are shown in FIGS. 6 to 11.

Figure 6:
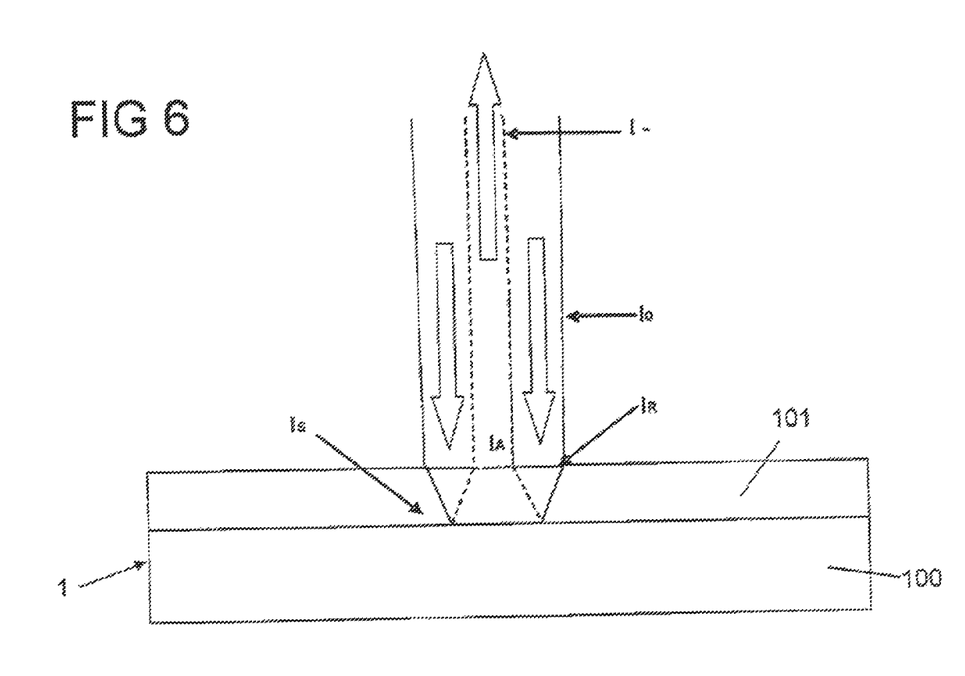
FIG. 6 shows a reduction of the intensity of monochromatic light by an oil film.

FIG. 6 shows a schematic illustration of the reduction of the intensity of monochromatic light by an oil film 101 on a sheet metal strip 100 of a sample 1. Monochromatic light, for example, a laser beam, having the starting intensity $I_0$, is oriented onto the sample 1. The intensity of the monochromatic light is reduced by the layer-thickness-dependent absorption $I_A$ of the oil film 101, the reflection IR at the interface of the surface of the oil film 101, and the interface between the oil film 101 and the surface of the sheet metal strip 100 and by the scattered light $I_S$ of the coating.

Figure 7:
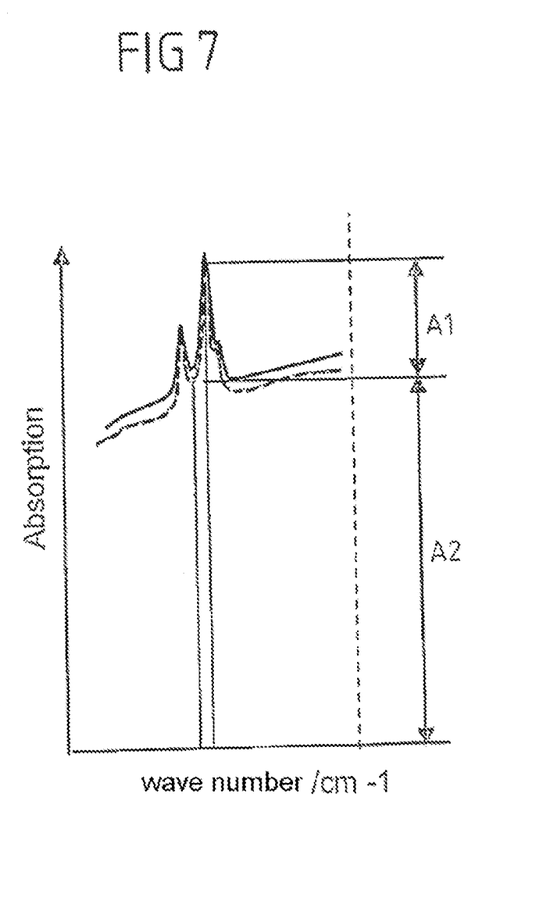
FIG. 7 shows a schematic illustration of the reduction of the layer thickness by absorption spectroscopy.

FIG. 7 shows, in a schematic illustration of the absorption over the wavelength, the reduction of the layer thickness by the absorption spectroscopy of the arrangement according to FIG. 6.

FIG. 7 shows the peak $A_1$, which represents the layer-thickness dependent absorption $I_A$ of the oil film 101, and, with $A_2$, the reduction of the intensity of the monochromatic light by the reflection at the surface of the oil film 101, by the scattered light of the coating, and the reflection of the interface between the oil film 101 and the sheet metal strip 100.

Figure 8:
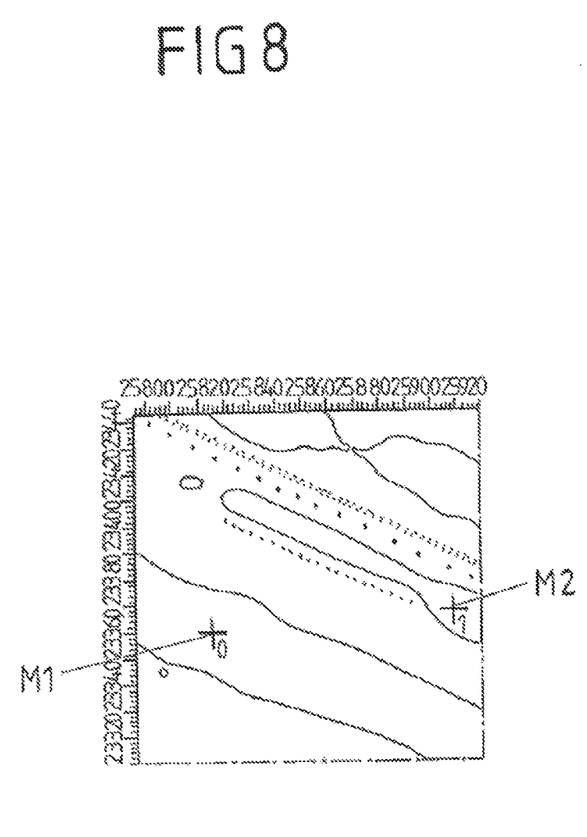
FIG. 8 shows a schematic illustration of a sample having a grease layer located on the sample surface.
Figure 9:
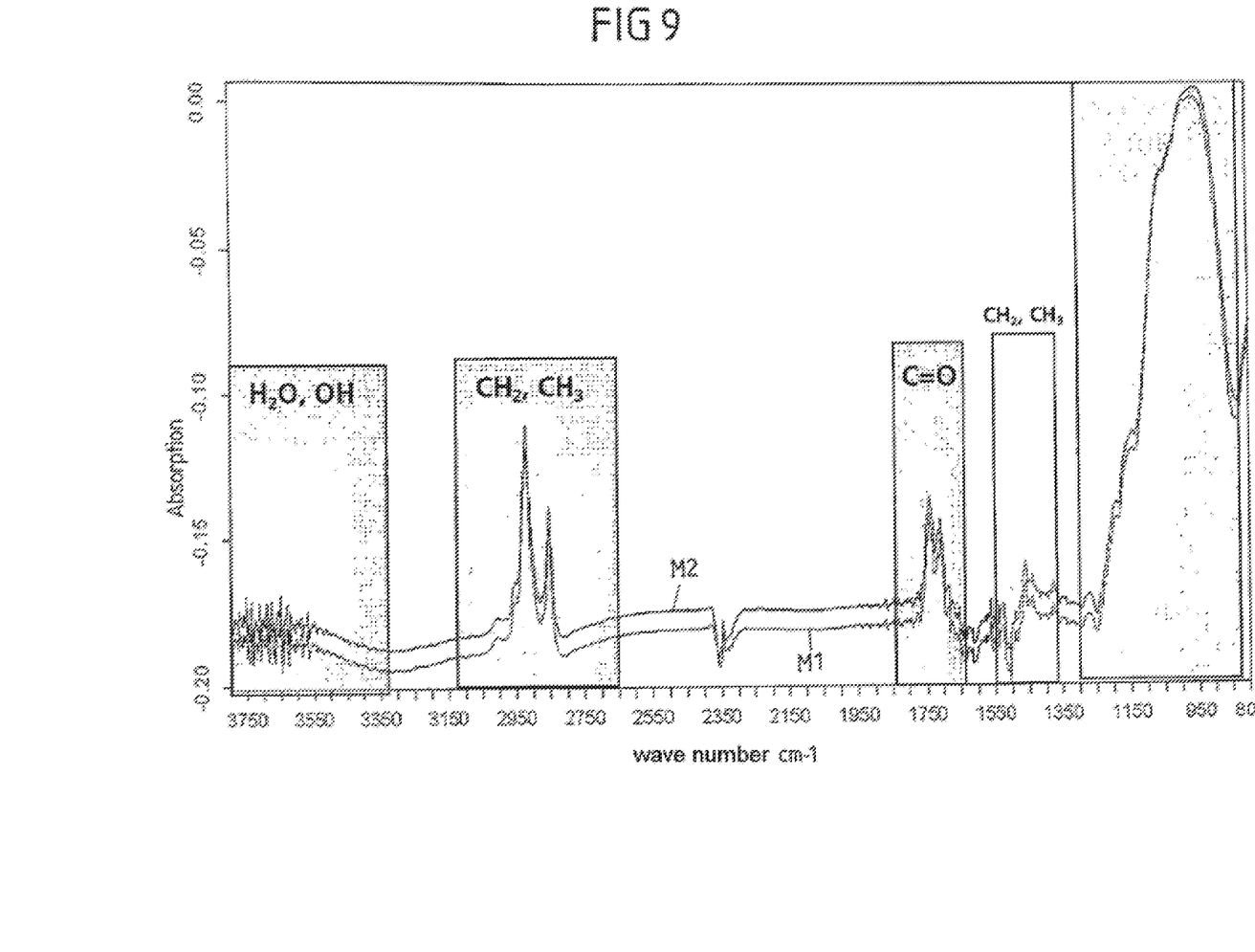
FIG. 9 shows a schematic illustration of the absorption bands over the wavelength of a measurement of the sample surface at two selected measurement points using a spectroscope.

FIGS. 8 and 9 illustrate an example of a measurement using a spectroscope. A plate, which is schematically shown in FIG. 8, having a grease layer located thereon and two measurement points $M_1$ and $M_2$, is used as the sample.

FIG. 9 shows two spectra, which were measured on the plate sample having a grease layer at the two measurement points $M_1$ and $M_2$ on the plate sample. In the diagram according to FIG. 9, the absorption peaks are shown with the associated functional groups.

In addition to the broad, strong absorption peak at approximately 1 000 cm$^{-1}$, further absorption peaks occur at approximately 1 500 cm$^{-1}$ (methylene $CH_2$ and methylene $CH_2$ and methyl $CH_3$), at approximately 1 750 cm$^{-1}$ (ketone C=O), 2 700 cm$^{-1}$, and 3 000 cm$^{-1}$. A broad absorption peak occurs between 3 700 cm$^{-1}$ and 3 350 cm$^{-1}$ ($H_2O$ and OH). These additional peaks may all be attributed to the presence of the grease layer, the absorption peak of the OH group can originate from the grease or from the ambient humidity, which has accumulated on the plate surface.

The absorption over the wave number, as illustrated in FIG. 9, at the two measurement points $M_1$ and $M_2$ according to FIG. 8 shows the peaks typical for specific materials in a wave number range between 800 and 3 750 cm$^{-1}$. At 2 850 cm$^{-1}$ and at 2 900 cm$^{-1}$, the characteristic bands for finger trace grease can be recognized. In the case of a finger trace scan, preferably only these bands are analyzed, but not the entire absorption band over a range of 1-10 μm wavelength.

Figure 10:
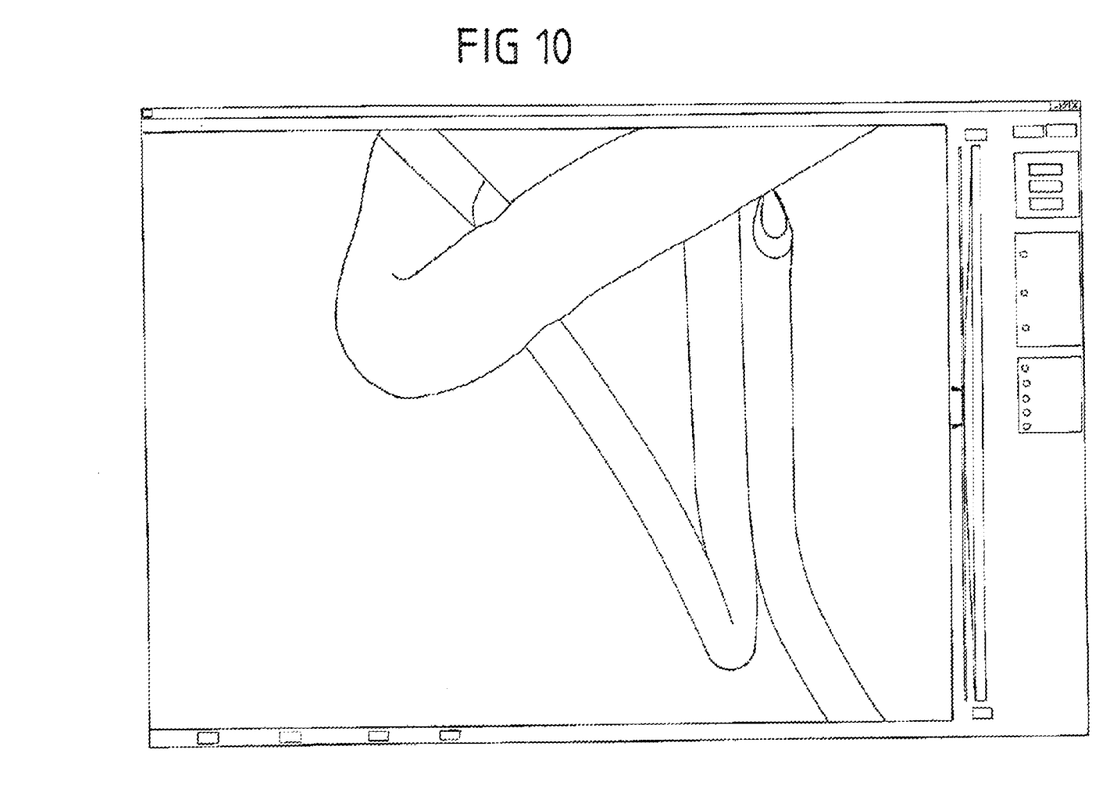
FIG. 10 shows a schematic, two-dimensional illustration of an intensity image.

FIG. 10 shows a two-dimensional illustration of an intensity image, having the illustration of the respective X/Y position of each pixel and the intensity of each pixel depicted by means of a grayscale illustration, so that a structural illustration of the surface of the sample results therefrom.

Figure 11:
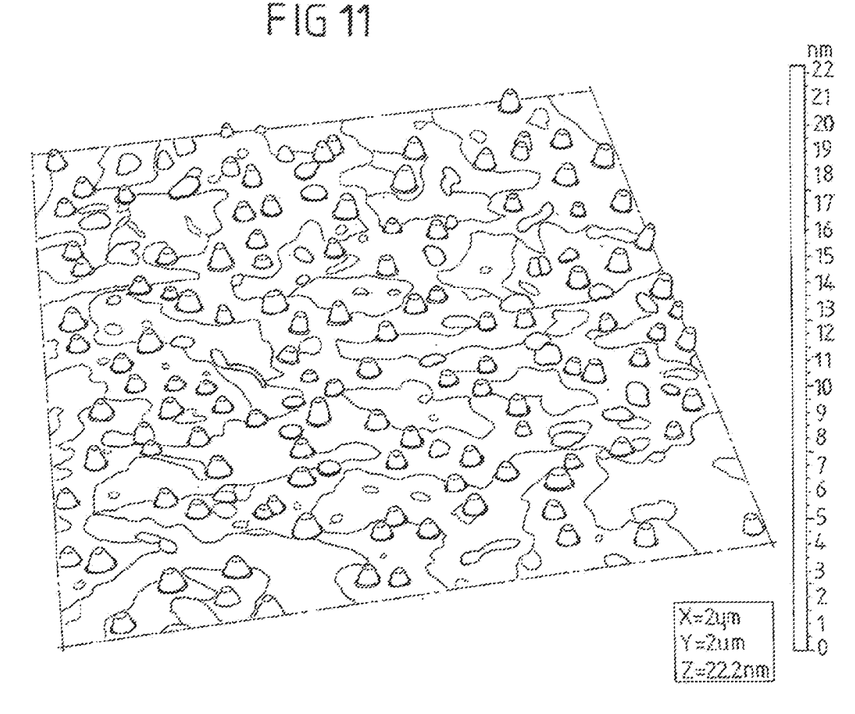
FIG. 11 shows a schematic, three-dimensional illustration of an intensity image.

FIG. 11 shows an imaging, three-dimensional illustration of the intensity image of each individual measurement point on the sample surface and a scale, which is illustrated schematically adjacent thereto, of the spectral intensity, which is preferably applied in color and corresponds to the respective color of the measurement points, so that in addition to a qualitative judgment of the sample surface, a quantitative judgment is also possible. The topography, which is shown in FIG. 11 in grayscale, can be two-dimensional as shown in the figure, but also three-dimensional with the substance S located thereon, as illustrated in FIG. 12.

Figure 12:
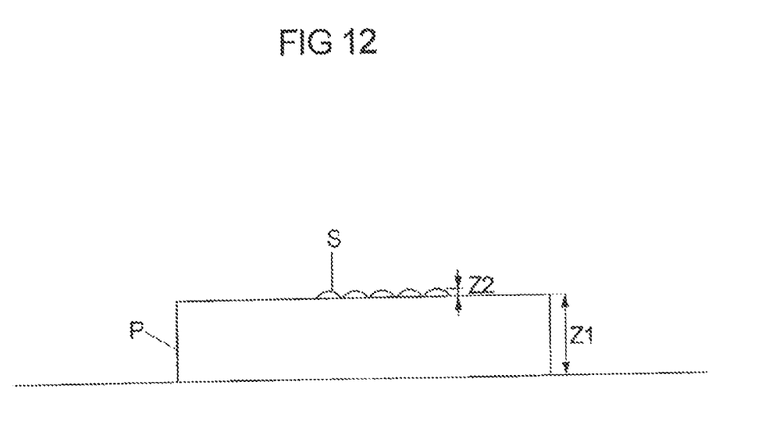
FIG. 12 shows a schematic, three-dimensional illustration of an object as grayscale and the chemical substance located on the surface in a color illustration.

FIG. 12 shows a schematic, two-dimensional illustration of a sample P having the height profile Z1 of the sample P as grayscale and the chemical substance S, which is located on the surface of the sample P, having the height profile Z2, for example, in a red scale illustration. As a function of the height Z2 of the substance S, it can be displayed in a color palette from light red to dark red in a two-dimensional image.

Using the scanning method according to the invention and the scanning device derived therefrom, a technology is implemented which enables a shading-free and distortion-free recording of the sample surface using a single scanning procedure, in that
 a distance image,
 an intensity image,
 optionally an RGB image if an RGB sensor is arranged for ascertaining the color values of the measured points
are prepared at a distance resolution of approximately 1 mm, in particular less than or equal to 0.1 mm, wherein each scanned pixel supplies image and distance information. Furthermore, the method according to the invention and the device according to the invention ensure the suppression of background light, so that a reliable function of the scanning method is also ensured in the event of external light.

LIST OF REFERENCE NUMERALS 1 sample receptacle
2 scanning unit
3 analysis unit
4 X-Y axis deflection unit
5 Z axis drive unit
7 RGB image recording unit (RGB sensor)
8 pulse generator
9 image display unit (display screen)
10 line
11 modulator
12 image recording photodiode
13 collimator
14 semitransparent mirror
15 polygonal deflection mirror
16 electric motor
17 correcting lens
18 redirection mirror
19 synchronization photodiode
20 circuit board
21 laser activation electronics
22 IR laser light source
23 transmitting lens
24 lock-in signal amplifier
25 photodiode receiver
26 receiving lens
27 time or phase measurement unit
28 digital output
29 analog output
30 central computer unit (CPU)
40 X-Y axis driver unit
50 Z axis driver unit
61 memory unit
62 external memory unit
91, 92 IR detectors
93, 94 objective
100 sheet metal strip
101 oil film
300 microprocessor
$A_1$, $A_2$ peaks
I transmitted light
$I_A$ layer-thickness dependent absorption
$I_0$ starting intensity
$I_R$ reflection
$I_S$ scattered light
L emitted laser beam
$M_1$, $M_2$ measurement points and curves
R reflected laser beam
S substance P sample or measured object Δφ phase shift or phase difference

The invention claimed is:

1. A method for detecting the surface structure and composition of a sample by means of a scanning unit wherein the sample and the scanning unit are moved in relation to one another,
wherein
a sample surface is irradiated line-by-line using a laser beam emitted from the scanning unit, having predefined laser beam diameter in a step width corresponding to the laser beam diameter, and the reflected laser beam is detected and analyzed coaxially in relation to the emitted laser beam, the laser beam reflected from the sample surface is detected and a digital image of the topography of the sample surface and the intensity of the reflected laser beam is generated from deviations of the reflected laser beam from the emitted laser beam and a run time, which is dependent on the distance of the scanning unit from the sample surface, of the laser beam, which is emitted from the scanning unit and reflected from the sample surface, is detected and analyzed to prepare a distance image corresponding to the topography of the sample surface.

2. The method as claimed in claim 1, wherein the laser beam is emitted at a wavelength which corresponds to a wavelength range of an absorption spectrum of a composition of the sample surface.

3. The method as claimed in claim 1, wherein the emitted laser beam is collimated to a laser beam diameter less than or equal to 1 mm.

4. The method as claimed in claim 1, wherein a thickness of internal layers of the sample, which differ from external layers, is analyzed.

5. The method as claimed in claim 1, wherein a phase shift between the laser beam emitted from the scanning unit and the laser beam reflected from the sample surface is detected and analyzed to ascertain the topography of the sample surface.

6. The method as claimed in claim 5, wherein the laser beam emitted from the scanning unit is sinusoidally modulated and, to determine the phase shift between the laser beam emitted from the scanning unit and the laser beam reflected from the sample surface, the reflected laser beam detected by the scanning unit is correlated with a reference signal synchronous with the emitted laser beam.

7. The method as claimed in claim 1, wherein an absorption-related deviation of the laser beam reflected from the sample surface from the laser beam emitted from the scanning unit is analyzed to prepare an intensity image corresponding to a chemical substance on and in the sample surface.

8. The method as claimed in claim 7, wherein the sample surface is scanned serially point-by-point using the modulated laser beam and image elements of a digital image are emulated from the distance and intensity measurements arranged in a matrix.

9. The method as claimed in claim 1, wherein the reflected laser beam is detected by means of an RGB image recording unit to ascertain color values of the scanned sample surface.

10. A device for detecting the surface structure and composition of a sample, comprising:
a sample receptacle,
a scanning unit comprising
a laser light source for emitting a laser beam having a wavelength range of a known or previously ascertained significant absorption peak of a chemical substance or for ascertaining the significant absorption peak, a laser beam is tuned in a range of the infrared spectrum,
a receiver for receiving laser beams transmitted or reflected from a sample surface, and
an X-Y axis deflection unit, which scans the sample surface using the laser beams emitted from the laser source, and
an analysis unit comprising
a first computer unit for generating a topographic distance image of the sample surface having the chemical substance, the image being generated using a run time, which is dependent on the distance of the scanning unit from the sample surface, of the laser beam, which is emitted from the scanning unit and reflected from the sample surface, is detected and analyzed to prepare a distance image corresponding to the topography of the sample surface,
a second computer unit for generating an infrared image, which depicts an intensity of the reflected laser beams, of the sample surface having the chemical substance, and
a central computer unit which is bidirectionally connected to a data memory, an image display unit or display screen, and the first and second computer unit.

11. The device as claimed in claim 10, wherein the sample receptacle and/or the scanning unit is/are connected to a Z axis drive unit for changing a distance between the sample receptacle and the scanning unit, which is bidirectionally connected via the Z axis driver unit to the central computer unit.

12. The device as claimed in claim 10, further comprising an RGB image recording unit, which is oriented onto the sample surface, and which is bidirectionally connected via a third computer unit for generating an RGB image to the central computer unit.

13. The device as claimed in claim 10, wherein the laser source has an IR laser light source, a transmitting lens, which orients laser beams emitted from the IR laser light source onto the sample surface, and light source activation electronics for activating the IR laser light source.

14. The device as claimed in claim 10, wherein the light receiver has an IR photodiode receiver, a receiving lens, which is arranged on the receiving side receiving the reflected laser beams, and a lock-in signal amplifier, which amplifies the signals emitted from the IR photodiode receiver.

15. The device as claimed in claim 10, wherein a pulse generator activates light source activation electronics, a lock-in signal amplifier, and the three computer units.

16. The device as claimed in claim 10, wherein the IR laser light source directs an IR laser beam via a modulator, which is activated by laser activation electronics, onto a collimator, which emits the IR laser beam having limited laser beam diameter onto a deflection unit, which deflects the IR laser beam line-by-line onto the sample and deflects the IR laser beams reflected from the sample surface to an image recording photodiode.

17. The device as claimed in claim 16, wherein a semitransparent mirror is arranged in the beam path between the collimator and the deflection unit, which transmits the IR laser beams emitted from the collimator to the deflection unit, on the one hand, and deflects the IR laser beams, which are serially combined by the deflection unit and reflected from the sample surface, to the image recording photodiode.

18. The device as claimed in claim 16, wherein the IR laser beams, which are fanned out line-by-line by the deflection unit, and the reflected IR laser beams received from the deflection unit, are guided via a correcting lens and a redirection mirror to the sample.

19. The device as claimed in claim 16, wherein at least a part of the IR laser beams, which are fanned out line-by-line by the deflection unit, are deflected onto a synchronization photodiode.

20. The device as claimed in claim 16, wherein the deflection unit consists of a polygonal deflection mirror, which is driven by an electric motor, or a galvanometer.

* * * * *